US012778440B1

(12) United States Patent
Huang et al.

(10) Patent No.: US 12,778,440 B1
(45) Date of Patent: Nov. 3, 2026

(54) METHODS FOR COMPENSATING IMPEDANCE LOADING EFFECT ON ELECTRODE LOCATIONS

(71) Applicant: St. Jude Medical, Cardiology Division, Inc., St. Paul, MN (US)

(72) Inventors: Hai Huang, Woodbury, MN (US); Travis Dahlen, Forest Lake, MN (US); Ashish Bhargava, Woodbury, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 595 days.

(21) Appl. No.: 18/196,469

(22) Filed: May 12, 2023

Related U.S. Application Data

(60) Provisional application No. 63/349,317, filed on Jun. 6, 2022.

(51) Int. Cl.

| | |
|---|---|
| ***A61B 5/0538*** | (2021.01) |
| ***A61B 5/00*** | (2006.01) |
| ***A61B 34/20*** | (2016.01) |

(52) U.S. Cl.
CPC .......... *A61B 5/0538* (2013.01); *A61B 5/6852* (2013.01); *A61B 34/20* (2016.02);
(Continued)

(58) Field of Classification Search
CPC ..... A61B 5/0538; A61B 34/20; A61B 5/6852; A61B 2034/2051; A61B 2560/0223; A61B 5/065; A61B 18/1492; A61B 2034/301; A61B 2018/00875; A61B 5/6833; A61B 5/285; A61B 5/287; A61B 5/0215; A61B 5/029; A61B 5/0536; A61B 5/06; A61B 5/062; A61B 5/063; A61B 5/145; A61B 8/0833; A61B 18/20; A61B 2034/2046; A61B 2034/2053; A61B 2090/367; A61B 2090/3958; A61B 5/352; A61B 1/2733; A61B 5/0044; A61B 5/053; A61B 18/02; A61B 18/14; A61B 18/18; A61B 18/24; A61B 2017/00243; A61B 2017/00247;
(Continued)

(56) References Cited

U.S. PATENT DOCUMENTS

| | | | | |
|---|---|---|---|---|
| 10,299,753 | B2 * | 5/2019 | Govari | A61B 5/062 |
| 10,362,954 | B2 * | 7/2019 | de la Rama | A61B 5/6852 |

(Continued)

*Primary Examiner* — Adam Z Minchella
(74) *Attorney, Agent, or Firm* — Billion & Armitage

(57) ABSTRACT

A method of compensating for impedance loading effect in impedance-based location system includes determining a geometrical center for a grid of electrodes attached to a distal end of a catheter shaft, the catheter shaft further including at least one shaft electrode and an electromagnetic sensor; determining a first shift vector from the geometrical center to a longitudinal axis of the catheter shaft; determining a spline vector for the grid of electrodes; determining an angle between the spline vector and the longitudinal axis; determining a lateral grid shift vector using the first shift vector and the angle; determining a longitudinal grid shift vector extending from the geometrical center to a plane normal to the longitudinal axis and extending through the distal end; and applying the lateral grid shift vector and the longitudinal grid shift vector to each electrode of the grid of electrodes.

20 Claims, 16 Drawing Sheets

(52) U.S. Cl.
CPC ................. *A61B 2034/2051* (2016.02); *A61B 2560/0223* (2013.01)

(58) Field of Classification Search
CPC ........... A61B 2018/00392; A61B 2018/00702; A61B 2018/00839; A61B 2018/1253; A61B 2018/162; A61B 2560/0238; A61M 25/0147; A61M 25/0127; A61N 1/06; A61N 1/32; A61N 1/36564; A61N 1/403; A61N 1/00; A61N 1/3621; A61N 1/3627
See application file for complete search history.

(56) References Cited

U.S. PATENT DOCUMENTS

| | | | | |
|---|---|---|---|---|
| 10,750,975 | B2 | 8/2020 | Hill et al. | |
| 2012/0265054 | A1* | 10/2012 | Olson | A61B 34/20 600/424 |
| 2016/0367323 | A1* | 12/2016 | Malinin | A61B 34/20 |
| 2019/0350489 | A1* | 11/2019 | Ludwin | A61B 5/72 |
| 2020/0138525 | A1* | 5/2020 | Hill | A61B 5/6858 |
| 2021/0330213 | A1 | 10/2021 | Papini | |

* cited by examiner

METHODS FOR COMPENSATING IMPEDANCE LOADING EFFECT ON ELECTRODE LOCATIONS

CROSS-REFERENCE TO RELATED APPLICATIONS

This application claims the benefit of U.S. application No. 63/349,317, filed Jun. 6, 2022, which is hereby incorporated by reference in its entirety.

BACKGROUND

The present invention relates generally systems and methods for imaging/tracking a catheter or mapping a heart. More particularly, this disclosure relates to computer-implemented systems and methods for determining the position of electrodes arranged in a grid located at a distal end of a catheter, and/or determining the shape of an electrode array positioned at a distal end of a catheter.

SUMMARY

According to one aspect, a method of compensating for impedance loading effect in impedance-based location system includes determining a geometrical center for a grid of electrodes attached to a distal end of a catheter shaft, the catheter shaft further including at least one shaft electrode and an electromagnetic sensor; determining a first shift vector from the geometrical center to a longitudinal axis of the catheter shaft; determining a spline vector for the grid of electrodes; determining an angle between the spline vector and the longitudinal axis; determining a lateral grid shift vector using the first shift vector and the angle; determining a longitudinal grid shift vector extending from the geometrical center to a plane normal to the longitudinal axis and extending through the distal end; and applying the lateral grid shift vector and the longitudinal grid shift vector to each electrode of the grid of electrodes.

According to another aspect, a computer readable medium includes instructions for a method of compensating for impedance loading effect in impedance-based location system. The method includes determining a geometrical center for a grid of electrodes attached to a distal end of a catheter shaft, the catheter shaft further including at least one shaft electrode and an electromagnetic sensor; determining a first shift vector from the geometrical center to a longitudinal axis of the catheter shaft; determining a spline vector for the grid of electrodes; determining an angle between the spline vector and the longitudinal axis; determining a lateral grid shift vector using the first shift vector and the angle; determining a longitudinal grid shift vector extending from the geometrical center to a plane normal to the longitudinal axis and extending through the distal end; and applying the lateral grid shift vector and the longitudinal grid shift vector to each electrode of the grid of electrodes.

According to another aspect, a system includes a controller that performs the steps of a method of compensating for impedance loading effect in impedance-based location system. The method includes determining a geometrical center for a grid of electrodes attached to a distal end of a catheter shaft, the catheter shaft further including at least one shaft electrode and an electromagnetic sensor; determining a first shift vector from the geometrical center to a longitudinal axis of the catheter shaft; determining a spline vector for the grid of electrodes; determining an angle between the spline vector and the longitudinal axis; determining a lateral grid shift vector using the first shift vector and the angle; determining a longitudinal grid shift vector extending from the geometrical center to a plane normal to the longitudinal axis and extending through the distal end; and applying the lateral grid shift vector and the longitudinal grid shift vector to each electrode of the grid of electrodes.

DETAILED DESCRIPTION

The present invention relates generally to systems and methods for imaging/tracking a catheter or mapping a heart where the catheter includes an array/grid of electrodes attached to the distal end. Specifically, the present invention is directed to a system, a processor, and/or methods to compensate for location errors introduced by an impedance-based electrode location system. One source of location errors in impedance-based electrode location systems is variations in impedance between different electrodes, resulting in impedance shift errors of at least some of the electrodes relative to one another. Stated another way, assuming the two different types of electrodes were located at the same physical location, the impedance-based position location of each electrode would be different as a result of differences in impedance presented by each. Positional errors caused by impedance shifts may affect the visualization of the catheter. For example, a catheter having a shaft electrode and an array/grid of electrodes attached to a distal end of the shaft may result in errors in the position of the array/grid of electrodes relative to the shaft. In one aspect, the present disclosure provides a method of compensating for impedance shift errors. In some embodiments, this includes generating lateral and longitudinal grid shift vectors that are applied to the electrodes located on the array at the distal end of the catheter. The lateral and longitudinal grid shift vectors are determined by calculating a grid center (an imaginary point in space representing a center point of the array) and a spline vector (an imaginary vector representing a center spline of the array). The grid center (particularly if calculated based on grid electrodes located close to the distal end of the shaft where the grid/array connects to the shaft) is utilized to determine the offset in position of the grid electrodes as compared to the longitudinal axis of the shaft and the spline vector is utilized to determine how much of that offset is due to the position or bend of the array/grid relative to the shaft. The grid center is also utilized to determine the offset in position of the grid electrodes as compared to a plane perpendicular to the longitudinal axis of the shaft. The result are grid compensation values that can be used to correct the position of the grid electrodes.

Figure 1:
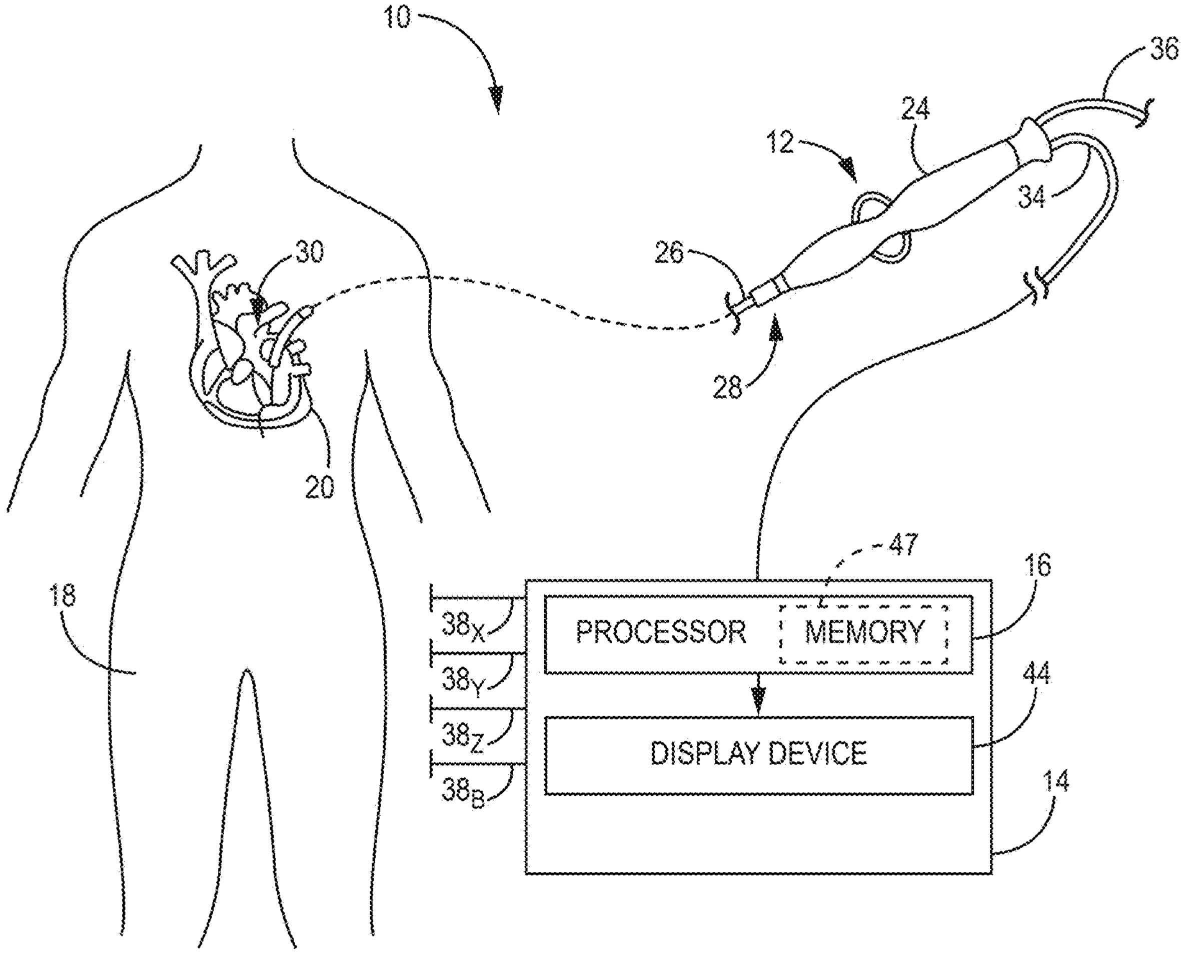
FIG. 1 is a schematic view of a medical system according to some embodiments.

Referring now to FIG. 1, an embodiment of medical system 10 utilized to treat a patient 18 is shown according to some embodiments. System 10 includes a processing system 14 and an electrophysiology catheter 12. In some embodiments, electrophysiology catheter 12 includes a proximal end 28, a shaft 26, and a distal end 30. A handle 24 is located at the proximal end and allows a technician to guide/steer the distal end 30 of the catheter 12 within the patient's vasculature, including within the patient's heart 20. At least one electrode for mapping, ablation, and/or navigation/tracking may be provided at the distal end region of the catheter 12. The processing system 14 includes a processor 16 with memory 47 and a display device 44. Processor 16 may include units for visualization, navigation/tracking, ablation, and/or mapping. The processing system 14 may be in electrical communication with the catheter 12, for example via cable 34. The processing system 14 may also be in electrical communication with patch electrodes 38 attached to the body of a patient 18.

Units for navigation/tracking may include a unit for electromagnetic (EM) navigation/tracking and a unit for impedance navigation/tracking, discussed in more detail below. The patch electrodes 38 may form a part of an impedance-based electrode location system. Pairs of patch electrodes $\mathbf{38}_X$, $\mathbf{38}_Y$, $\mathbf{38}_Z$ are placed on the body along a first (x) axis, a second (y) axis, and a third (z) axis. Excitation of patch electrodes pairs $\mathbf{38}_X$, $\mathbf{38}_Y$, $\mathbf{38}_Z$ generates orthogonal electric fields within an area of interest of the body, such as the heart 20. Patch electrode 38B may be attached to the stomach of the patient 18. Catheter 12 includes one or more electrodes (shown in FIGS. 2A, 2B) that are utilized to detect and measure the electric fields generated via excitation of the patch electrode pairs $\mathbf{38}_X$, $\mathbf{38}_Y$, $\mathbf{38}_Z$. The processing system 14 utilizes the measured impedances to determine the location of one or more of the electrodes—referred to herein as an impedance-based electrode location system. In addition, the electromagnetic navigation/tracking unit may include one or more magnetic coils located external to the patient and utilized to generate one or more—typically orthogonal—magnetic fields in the area associated with the patient 18. Catheter 12 includes one or more sensors configured to detect one or more of the magnetic fields. The processing system 14 utilizes the measured magnetic fields to determine the location of one or more of the sensors—referred to herein as a magnetic-based location system.

Figure 2A:
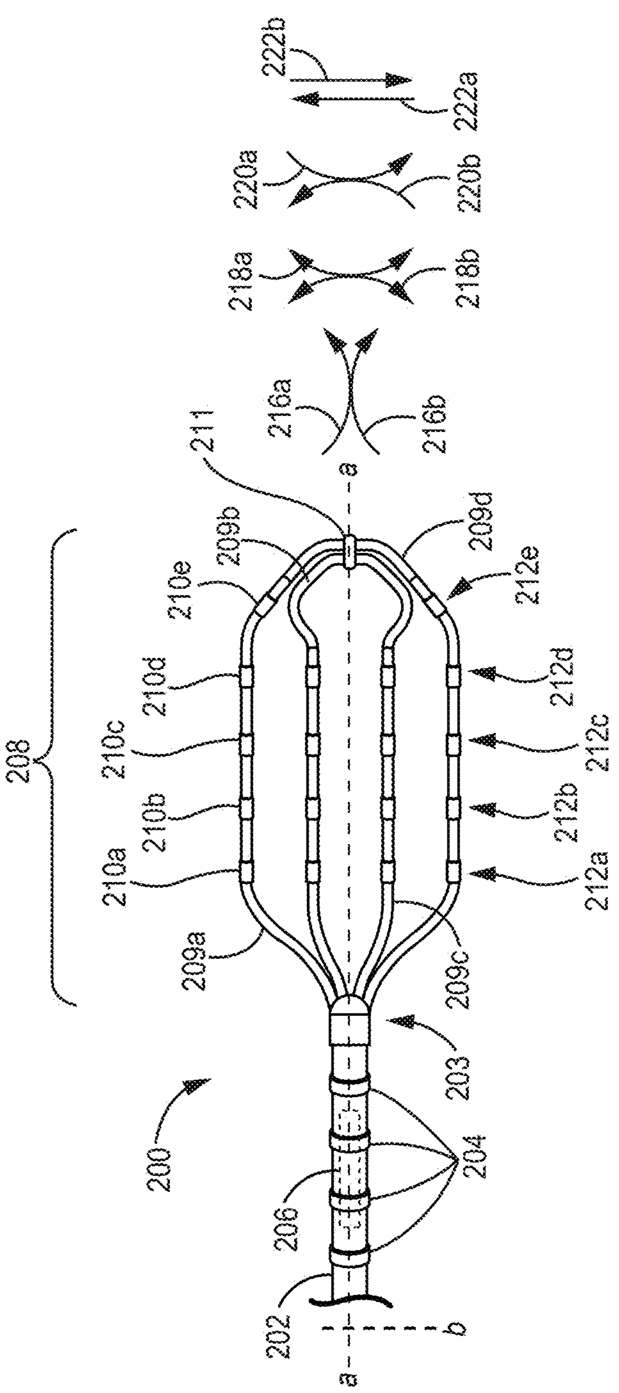
FIG. 2A is a plan view of a catheter with a grid of electrodes attached to the distal end of the shaft according to some embodiments.
Figure 2B:
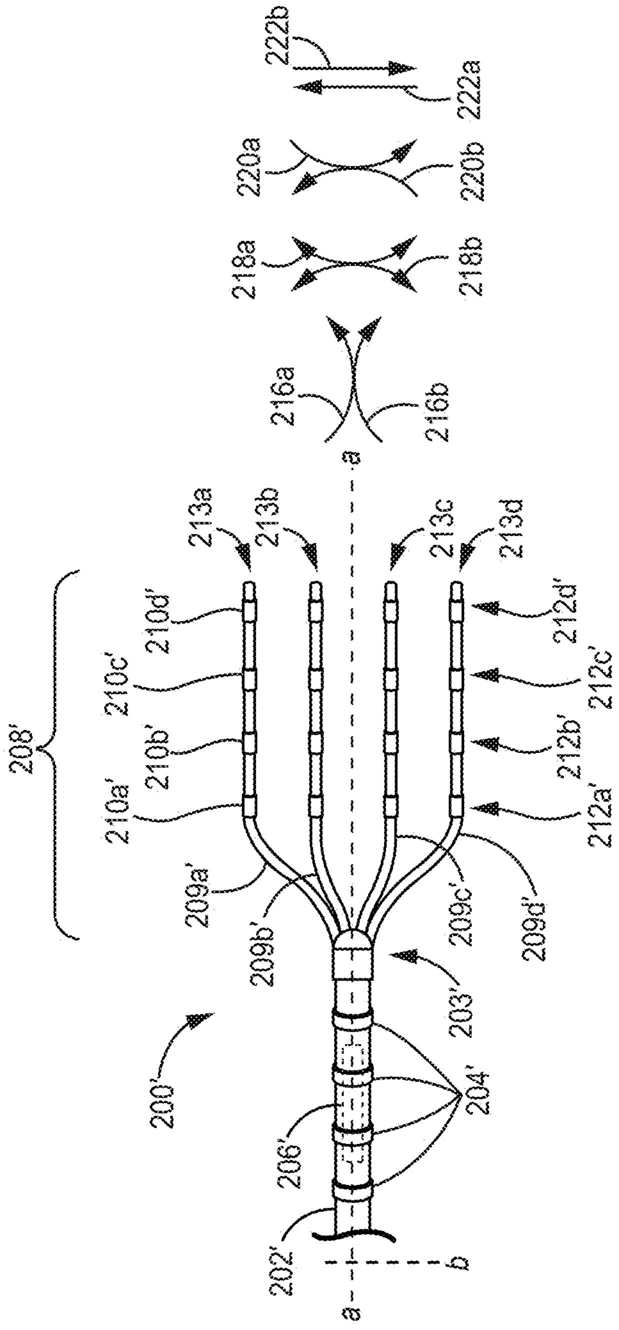
FIG. 2B is a plan view of a catheter with a grid of electrodes attached to the distal end of the shaft according to some embodiments.

Referring now to FIGS. 2A and 2B, which are plan views of different embodiments of catheter 12 having a grid/array 208 (208' in FIG. 2B) of electrodes 210, 210' located at the distal end. The catheter embodiment illustrated in FIG. 2A is disclosed in commonly owned U.S. patent application Ser. No. 17/237,279 (published as US 2021/0330213), the entire disclosure is incorporated by reference. Catheter 200 includes a longitudinal axis a, a shaft 202 with a distal end 203, shaft electrodes 204, a location sensor 206, an array 208 comprised of a plurality of struts 209*a*, 209*b*, 209*c*, and 209*d* (collectively struts 209), and a plurality of electrodes 210*a*, 210*b*, 210*c*, 210*d*, and 210*e* (referred to collectively as electrodes 210). Likewise, the catheter 200' shown in FIG. 2B includes a longitudinal axis a, a shaft 202' with a distal end 203', shaft electrodes 204', a location sensor 206', an array 208' comprised of a plurality of struts 209*a*', 209*b*', 209*c*', and 209*d*' (collectively struts 209'), and a plurality of electrodes 210*a*', 210*b*', 210*c*', and 210*d*' (collectively electrodes 210').

With respect to the embodiment shown in FIG. 2A, the shaft includes a plurality of shaft electrodes 204 positioned along an outer surface of shaft 202. In the embodiments shown in FIG. 2A, four shaft electrodes 204 are shown, but in other embodiments fewer or greater shaft electrodes may be positioned along the shaft 202. In some embodiments, the geometry/size of the shaft electrodes varies from the electrodes 210 included on the array 208. For example, in some embodiments, the shaft electrodes 204 may be larger than the electrodes 210 and may have a width greater than the width of electrodes 210. In some embodiments, the location sensor 206 is positioned within the shaft. In the embodiments shown in FIGS. 2A and 2B, the location sensor 206 is positioned between two of the shaft electrodes 204. In some embodiments, the location sensor 206 is an electromagnetic (EM) sensor comprising a coil configured to detect magnetic fields.

In the embodiments shown in FIGS. 2A and 2B, the plurality of electrodes 210 of the array 208 is arranged in a grid formed by the plurality struts 209. The framework for grid 208 may be formed by any number and/or arrangement of struts 209. In the embodiment shown in FIG. 2A, the array 208 comprises struts 209*a*, 209*b*, 209*c*, and 209*d* extending from the distal end 203. In some embodiments, struts 209*a* and 209*d* are connected at a distal end to form an outer loop. Likewise, struts 209*b* and 209*c* are connected at a distal end to form an inner loop. In some examples, the struts 209*a*, 209*b*, 209*c*, and 209*d* lie in the same plane, wherein grid 208 may be described as a planar array. In the embodiment shown in FIG. 2B, the struts 209*a*', 209*b*', 209*c*' and 209*d*' similarly extend from the distal end 203' but are not connected at a distal end. In other words, the struts 209 have free ends 213. The struts 209*a*', 209*b*', 209*c*' and 209*d*' may similarly be described as a planar array. In the embodiments shown in FIGS. 2A and 2B, the struts 209*a*, 209*b*, 209*c*, and 209*d* lie in a same plane as the longitudinal axis a. In other embodiments, the struts 209*a*, 209*b*, 209*c*, and 209*d* do not lie in a same plane as the longitudinal axis a—in other words, the grid 208 is offset from the longitudinal axis a. The catheter 12 may have at least one grid 208 that is offset from the longitudinal axis a. In one example, the catheter 12 comprises a single grid 208 offset from the longitudinal axis a. In another example, the catheter 12 comprises two grids 208 each offset set from the longitudinal axis a—in other words, the grids 208 flank the longitudinal axis a.

Each of the struts 209, 209' includes a plurality of electrodes 210, 210'. In the embodiment shown in FIG. 2A, struts 209*a* and 209*d* include five grid electrodes 210*a*, 210*b*, 210*c*, 210*d*, and 210*e* and struts 209*b* and 209*c* include four grid electrodes 210*a*, 210*b*, 210*c*, and 210*d*. The electrodes 210 are organized into a plurality of columns 212, each column including an electrode affixed to at least one of the struts 209. In other words, each column 212 has at least one electrode 210. For example, in the embodiment shown in FIG. 2A, the array 208 has a proximal column 212*a* that includes four electrodes 210*a*—one located on each strut 209*a*, 209*b*, 209*c*, and 209*d*-spaced along an axis transverse to the longitudinal axis. In addition, array 208 includes a plurality of columns 212*b-e* distal to the proximal column 212*a*, each having a plurality of electrodes 210*b-e*. In the embodiment shown in FIG. 2A, the most distal column 212*e* includes two electrodes 210*e*. As described in more detail below, the electrodes 210*a* located in the proximal row are distinguished from the more distally located electrodes in part because the position of electrodes 210*a* can be more precisely known than the position of the more distally located electrodes 210*b*, 210*c*, 210*d*, and 210*e*. Likewise, in the embodiment shown in FIG. 2B, each of the plurality of struts 209*a*', 209*b*', 209*c*', and 209*d*' include four electrodes. The electrodes 210' are arranged in a plurality of columns 212' that each includes four electrodes 210'—one located on each strut 209*a*', 209*b*', 209*c*' and 209*d*'—spaced along an axis transverse to the longitudinal axis a.

In some embodiments, shaft electrodes 204 and/or grid electrodes 210 may be utilized to measure the electric field generated via excitation of the patch electrode pairs $\mathbf{38}_X$, $\mathbf{38}_Y$, $\mathbf{38}_Z$. The measured signals may be utilized to determine the x-y-z position of the plurality of electrodes 204, 210. In addition, EM sensor 206 may be utilized to measure the magnetic field generated by the external coils. The magnetic field measured by the EM sensor 206 may likewise be utilized to determine the x-y-z position of the EM sensor 206 and in turn the x-y-z-position of the shaft electrodes 206 and/or the grid electrodes 210. However, the ability to utilize the location/orientation information provided by the EM sensor 206 to inform on the x-y-z position of electrodes 210 decreases the more distal the electrodes are from the EM sensor 206. For example, the position/orientation information provided by the EM sensor 206 may be more beneficial in correcting/modifying the position estimates of the shaft electrodes 204 and/or the first column of grid electrodes 210*a*, 210*a*'. This is more prevalent in embodiments in which the array 208, 208' is capable of bending/twisting about various axes.

For example, arrows 216, 218, 220, and 222 in FIGS. 2A and 2B illustrate ways the array 208, 208' can bend, curve, and/or twist relative to the longitudinal axis a. These types of movements of the grid 208 needs to be accounted for when correcting for a shift in the impedance based measurements of the grid electrodes 210 (and in particular the distally located grid electrodes).

Arrows 216*a* and 216*b* illustrate the array 208 undergoing pitch—i.e., bending into and out of the page about an axis b transverse to the longitudinal axis a. For example, if the array 208 shown in FIG. 2A were to experience pitch, the distal end 211 of the array 208 would point into the page (away from the viewer—arrow 216*a*) or out of the page (towards the viewer—arrow 216*b*). For the array 208' shown in FIG. 2B, the free ends 213 would point into the page (away from the viewer—arrow 216*a*) or out of the page (towards the viewer—arrow 216*b*).

Arrows 218*a* and 218*b* illustrate the array 208, 208' curving into and out of the page respectively. In one example of the array 208 curving into the page, arrow 218*a*, strut 209*a* and strut 209*d* are positioned below the plane of the page (farther from the viewer) while struts 209*b* and strut 209 *c* are positioned in the plane of the page (closer to the viewer). In one example of the array 208 curving out of the page, arrow 218*b*, struts 209*a*, 209*d* are positioned above the plane of the page (closer to the viewer), and struts 209*b*, 209*c* are positioned in the plane of the page (farther from the viewer). Likewise, in the array 208' shown in FIG. 2B, struts 209'*a*, 209'*d* would be positioned below the plane of the page (farther from the viewer) when the array 208' is curved into the page and positioned above the plane of the page (closer to the viewer) when the array 208' is curved out of the page.

Arrows 220*a* and 220*b* illustrate the array 208, 208' undergoing roll—i.e., twisting about the longitudinal axis a. For example, when the array 208, 208' rolls, strut 209*a*, 209'*a* moves out of the page towards the viewer, while strut 209*d*, 209'*d* moves into the page away from the viewer.

Arrows 222*a* and 222*b* illustrate the array 208, 208' undergoing yaw—i.e., bending up and down with respect to the page. For example, when the array 208 bends upwards, arrow 222*a*, the struts 209*a-d* move upwards by pivoting relative to the distal end 203 of the shaft 202—strut 209*a*, 209'*a* would move upwards away from the longitudinal axis a and strut 209*d*, 209'*d* would move upwards towards the longitudinal axis a. In other words, as the array 208 bends upwards, the distal end of the array 208 moves up from the longitudinal axis a, and the struts 209*a-d*, 209'*a-d* are oriented at a positive angle to the longitudinal axis a. The opposite motion occurs when the array 208 bends downwards, arrow 222*b*—the distal end of the array 208 moves down from the longitudinal axis a, and the struts 209*a-d*, 209'*a-d* are oriented at a negative angle to the longitudinal axis a.

Figure 3:
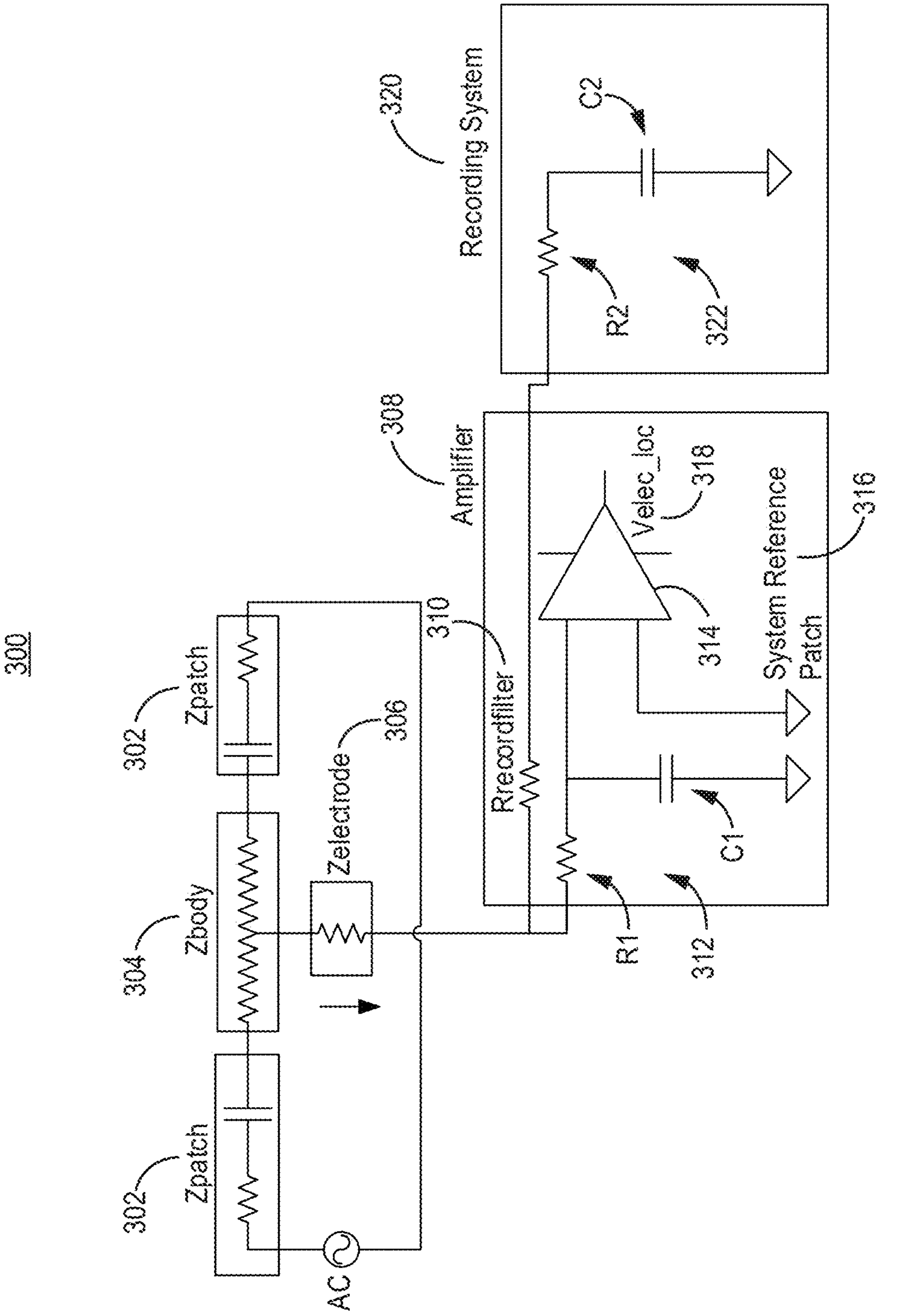
FIG. 3 is a simplified circuit diagram of an impedance-based catheter tracking system according to some embodiments.

FIG. 3 provides a simplified circuit 300 to illustrate a theory of operation of an impedance-based electrode location/tracking system. The circuit includes Z-patches 302 representing the impedance of the patch to skin interface, a Z-body 304 representing the impedance of the body, a Z-electrode 306 representing the impedance of the catheter electrode, an amplifier 308, and a recording system 320. The amplifier 308 includes a record filter 310, a resistor R1 and a capacitor C1 forming a resistor-capacitor (RC) circuit 312 at the front end of an amp 314, and a system reference patch 316. Record filter 310 represents the impedance of the amplifier filter to prevent the current from shunting to the recording system 320. The RC circuit 312 at the front end of the amp 314 may be used for defibrillation detection. Velec_loc 318 is the measured voltage from the catheter electrode. The recording system 320 includes a resistor R2 and a capacitor C2 forming an RC circuit 322.

An impedance-based catheter tracking system drives constant alternating current between patch pairs, e.g., $\mathbf{38}_X$, $\mathbf{38}_Y$, $\mathbf{38}_Z$, in the X (left-right), Y (chest-back), and Z (neck-left leg) axes, to produce three orthogonal electrical fields. Typically, an 8 kHz alternating current is utilized. The body/blood pool acts as a resistor (represented by Zbody

304) and the catheter electrodes, e.g., 204, 210, act as "voltage meters". The measured voltage on a catheter electrode varies relative to the system reference patch, e.g., $\mathbf{38}_B$, as the catheter moves along the axes. A system reference patch, e.g., $\mathbf{38}_B$, is typically provided on the stomach. The system reference patch has an initial location of (0, 0, 0).

In an ideal circuit, the RC circuit 312 provides infinite resistance to ground at 8 kHz and the determined location of a catheter electrode would be precise. However, because the input impedance to the measurement system is not infinite, each electrode will draw a tiny current from the system to be measured. As the Z-electrode 306 increases, the voltage drop across the electrode is higher. Based on ohms law, the voltage drop is proportional to the input impedance of the amplifier 308. In other words, the reduced input impedance to the amplifier 308 increases the loading effect on the voltage measured by an electrode. Additionally, the input impedance of the amplifier 308 is affected by the recording system 320. For example, each recording system has a different input impedance at 8 kHz. Furthermore, the recording system 320 provides another current path from the electrode to the recording system 320. Additionally, other components connected to the system may affect the input impedance of the system. When input impedance decreases, the current flowing through the electrode increases, which increases the voltage drop across the electrode.

Electrode size is another factor affecting the amount of impedance. For example, shaft electrodes 204, which are larger than the grid electrodes 210, have a lower impedance than grid electrodes 210. As one example, the impedance of a grid electrode 210 may be 2-3× greater than the impedance of a shaft electrode 204. Electrodes with different sizes have different amounts of loading effect on a measurement, such that the impedance-based location of the electrode will vary based on the type of electrode (e.g., impedance) utilized to make the measurement.

Figure 13:
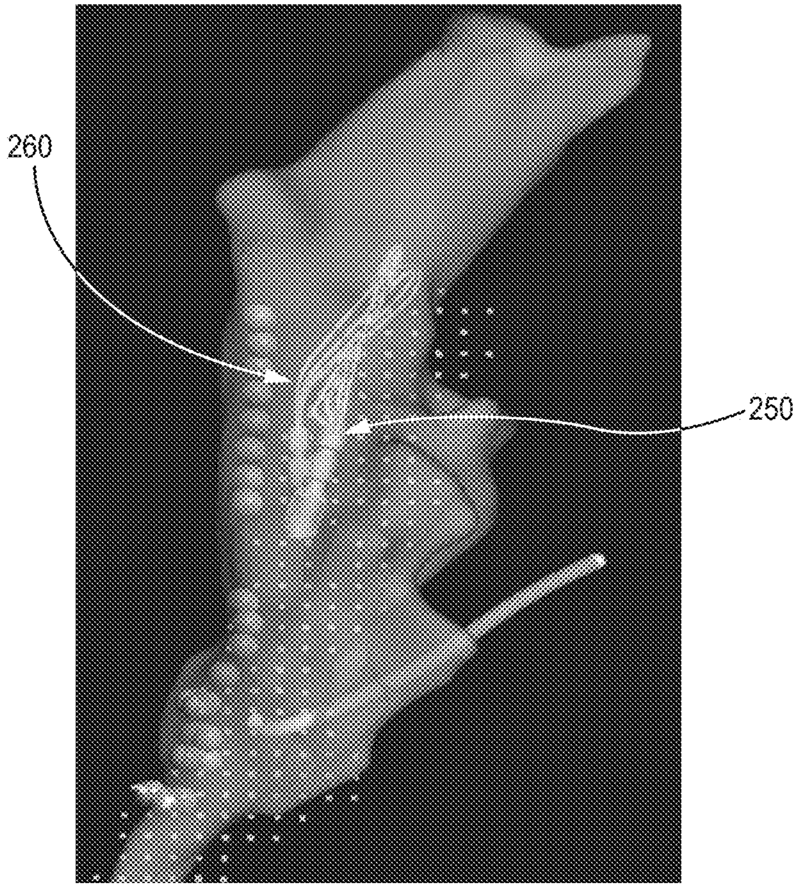
FIG. 13 is a view of a catheter with a grid electrode illustrating the spatula shape caused by the impedance shift and the shape of the catheter shown to the user without application of method 400 illustrated in FIG. 4, according to some embodiments

These differences in impedance and impedance loading exhibit as shifts from the shaft axis and can occur in the x, y, and/or z directions. Shifts in position may affect the visualization of the catheter. For example, the catheter may appear to have a spatula shape 250 (as shown in FIG. 13), wherein the larger shaft electrodes 204 present an impedance that results in an impedance-based location and the smaller grid electrodes 210 present an impedance that results in an impedance-based location that is offset or shifted from the position of the shaft electrodes due to the different impedance loading effects of the respective electrodes 204, 210. When this shift is not corrected, an incorrect shape 260 for the catheter may be display, as shown in FIG. 13 for example, where the array 208 is shifted away from the shaft axis a. In this example, the shape of the array 208, defined by the position of the electrodes 210 relative to one another, may be substantially accurate as each of the grid electrodes 210 has approximately the same impedance and therefore any impedance shift affects each grid electrode 210 approximately equally. However, the location/orientation of the array 208 relative to the shaft 202 may include impedance shift errors due to the differences in impedance between the shaft electrodes 204 and grid electrodes 210. However, because the grid electrodes 210 are approximately the same in size the shape of array 208 does not change because the impedance difference among grid electrodes 210 is negligible. As described in FIGS. 4-6, the present disclosure provides a method of compensating for impedance loading effects to provide more accurate impedance-based location estimates. Having an incorrect shape and/or location for the catheter may also affect the mapping of the heart. For example, the inaccuracy of the location of catheter electrodes may result in an inaccurate mapping of conductivity in the heart because the measurement is mapped to the wrong location.

Figure 4:
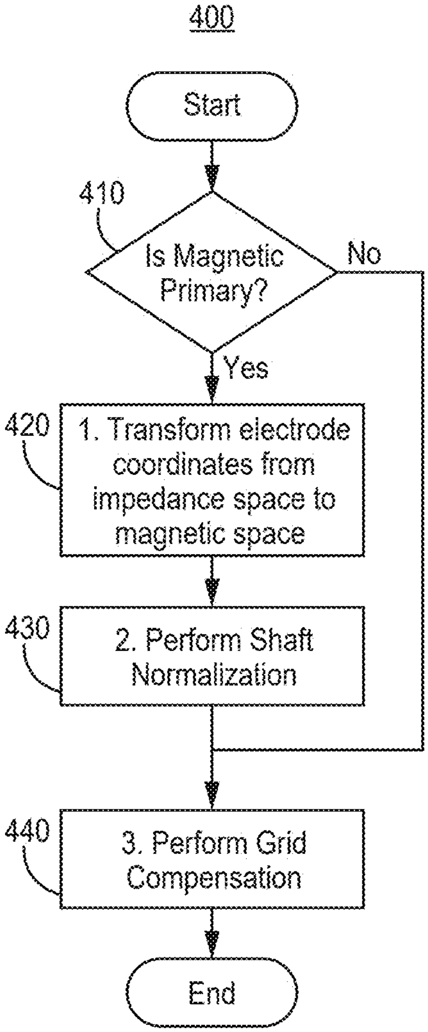
FIG. 4 is a flow chart of a catheter/grid localization method according to some embodiments.

Referring to FIG. 4, a flow chart of an exemplary implementation of a method 400 for correcting electrode position. In one aspect, method 400 compensates for shifts introduced by an impedance-based electrode location/tracking system. Thus, method 400 may be described as an impedance shift compensation method or an impedance loading effect shift compensation method. In another aspect, method 400 improves the accuracy of determining the shape of the electrode grid/array 208 of a catheter. In this context, method 400 may be included as part of an imaging method. In an additional aspect, method 400 improves the accuracy of determining the locations of electrodes carried by a catheter.

It is noted that equations and/or approaches in addition to, or alternative to the disclosed equations/approaches may be used to implement the steps of method 400. Additionally, although the description of method 400 refers to a catheter 200, 200' as shown in either of FIG. 2A or 2B, method 400 may be used with any electrophysiology catheter with electrodes arranged in an array/grid.

At Step 410, the operation mode of the catheter 200 is determined. The method of determining the position of the catheter—and in particular of the grid electrodes—is based primarily on position/orientation obtained from the electromagnetic (EM)-based measurements or the impedance-based measurements. An impedance-based position/orientation may be calculated, at least in part, on impedance position estimates obtained from impedance measurements from the shaft electrodes 204. Likewise, a magnetic-based position/orientation may be calculated based on magnetic-based estimates generated by the EM sensor 206. If catheter localization is magnetic primary, i.e., EM tracking, then method 400 proceeds to Step 420. If the operation mode is impedance primary, i.e., impedance tracking, then method 400 proceeds to Step 440.

If catheter localization is magnetic primary, then at Step 420 positions and axes in the impedance coordinate system are transformed to the magnetic coordinate system. For example, impedance positions/coordinates of all the grid electrodes 210, the shaft electrodes 204, distal shaft end 203, and/or shaft longitudinal axis are transformed from the impedance coordinate system to the magnetic coordinate system. As used herein, "a magnetic position or axis" is a position in the magnetic coordinate system determined by EM sensor 206 (e.g., a magnetic shaft longitudinal axis), "an impedance position or axis" is a position in the impedance coordinate system determined by the impedance system (e.g., an impedance shaft longitudinal axis), and "a transformed-impedance position or axis" is a position that has been transformed from the impedance coordinate system to the magnetic coordinate system (e.g., a transformed-impedance shaft longitudinal axis).

Figure 5:
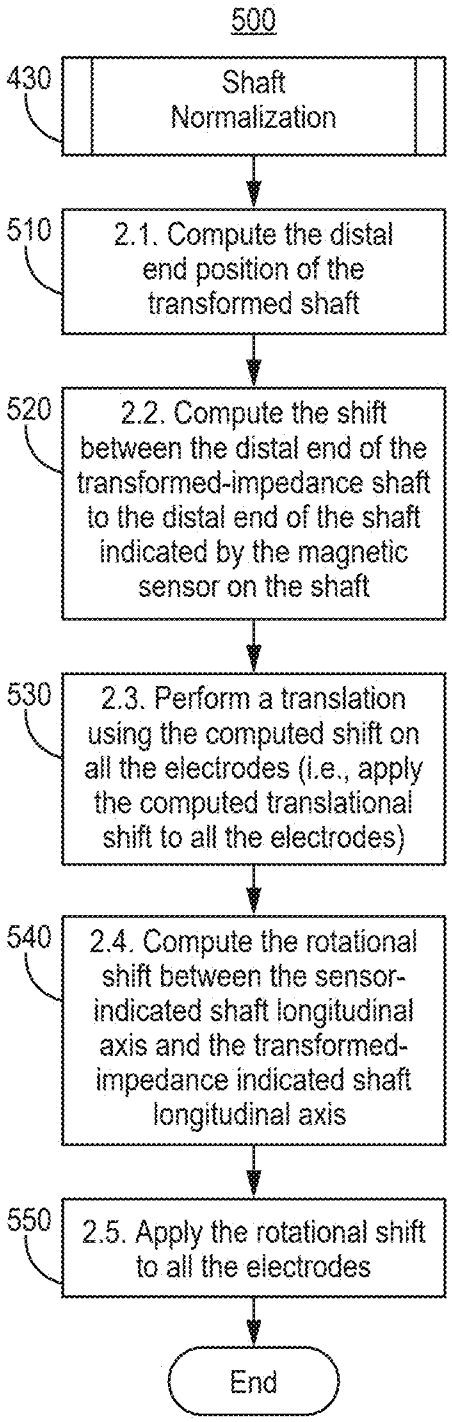
FIG. 5 is a flow chart of a shaft normalization method that may be used for the shaft normalization step of the method illustrated in FIG. 4 according to some embodiments.

At Step 430, shaft normalization/registration, described in more detail with respect to FIG. 5, is performed to harmonize the position/orientation of the shaft 202 as determined by impedance measurements with the position/orientation of the shaft 202 as determined by the EM measurements. In one aspect, shaft normalization/registration determines a translational shift vector for the shift between the transformed impedance position of the distal shaft end 203 and the magnetic position of the distal shaft end 203. The difference or offset between the transformed impedance position or axis of the distal end 203 and the magnetic-based position or axis of the distal end 203 may be utilized to determine the translational shift vector. In a further aspect, shaft normalization/registration determines a rotational shift vector between the transformed-impedance shaft longitudinal axis and the magnetic shaft longitudinal axis. The translational shift vector and the rotational shift vector produced by Step 430 are utilized to correct the positions of the electrodes determined based on the impedance measurements with the position information gleaned from the EM sensor 206. In some embodiments, the translational shift vector and the rotational shift vector are applied to the transformed impedance-based position estimates of the shaft electrodes 204 and/or grid electrodes 210 to correct the position estimates of the respective electrodes.

Figure 6:
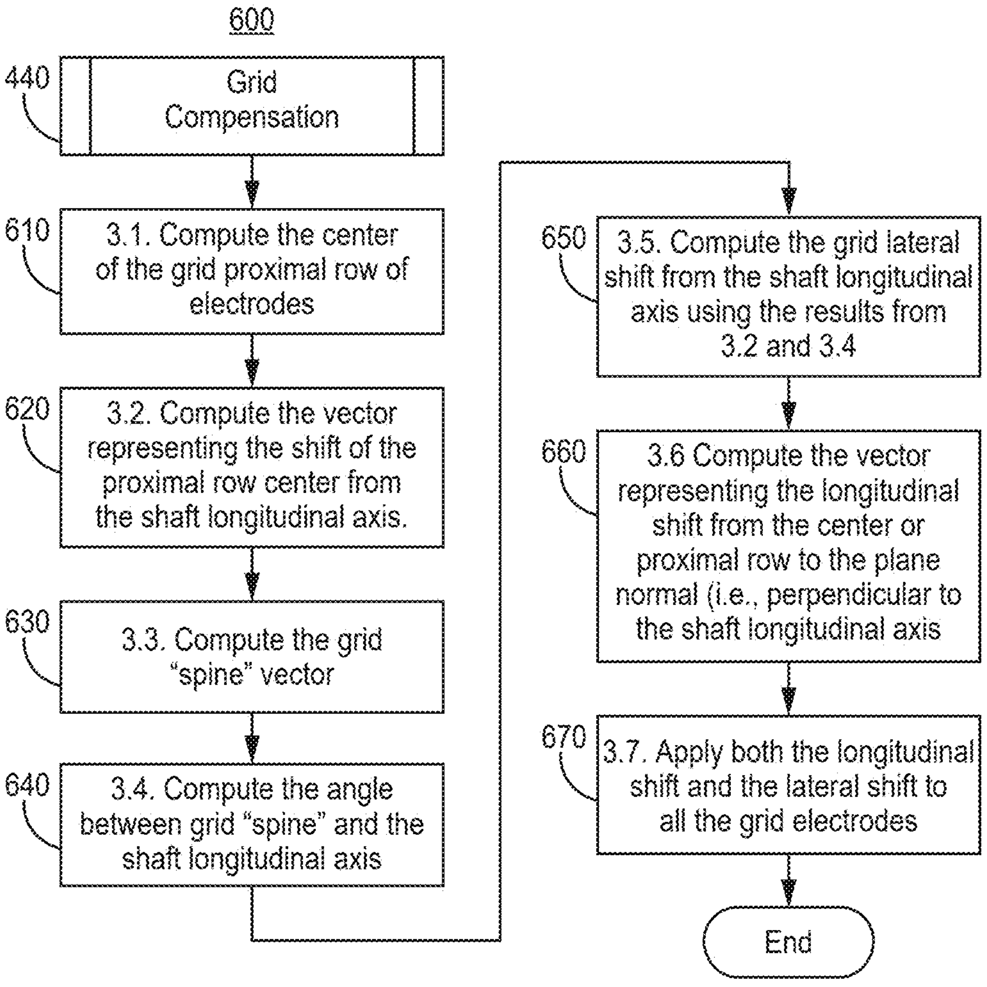
FIG. 6 is a flow chart of a grid compensation method that may be used for the grid compensation step of the method illustrated in FIG. 4 according to some embodiments.

At Step 440, grid shift compensation, described in more detail with respect to FIG. 6, is performed to compensate for lateral and longitudinal shifts of the grid 208 resulting from load effect errors described with respect to FIG. 3. In some embodiments, grid shift compensation only applies to the grid electrodes 210. In one aspect, grid shift compensation includes determining a shift between the grid electrodes 210 and the shaft electrodes 204 and then determines how much of that shift is attributable to a bend of the grid array 208 relative to the longitudinal axis of the shaft 202. In this way, the grid shift compensation provided at Step 440 avoids over-compensating the lateral and longitudinal shifts of the grid 208.

In some embodiments, grid shift vectors representing only the load effect errors (or impedance shift) are generated by calculating a grid center (an imaginary point in space representing a center point of the array) and a spline vector (an imaginary vector representing a center spline of the array). An offset between the longitudinal axis (in some embodiments, the impedance-based longitudinal axis) and the grid center represents a shift or offset between the shaft electrodes 204 and some average or combination of the grid electrodes 210. The spline vector represents an estimate of the angle between the shaft 202 and the grid array 208 grid center and can be utilized to determine how much of the offset is attributable to bending of the array 208 relative to the shaft 202 versus load effect errors, wherein the result is a lateral grid shift vector. Likewise, a longitudinal grid shift vector is generated that represents the shift of the grid center relative to a plane extending through the distal end of the catheter shaft and normal to the longitudinal axis of the catheter shaft. The lateral grid shift vector and the longitudinal grid shift vector produced by Step 440 form a second plurality of shift vectors that may be used to compensate for impedance shift of the grid.

Referring to FIG. 5, a flowchart of an exemplary method 500 for performing the shaft normalization, as described at Step 430 of method 400, is provided. In one aspect, method 500 establishes transformed-impedance positions for each grid electrode. 210. In one aspect, shaft normalization includes determining a translational shift between the magnetic longitudinal axis of the shaft and the transformed-impedance longitudinal axis of the shaft. In a further aspect, shaft normalization includes determining a rotational shift between the magnetic longitudinal axis of the shaft and the transformed-impedance longitudinal axis of the shaft. Although the exemplary shaft normalization method 500 illustrated in FIG. 5 determines the translational shift before the rotational shift, the rotational shift may be determined before the translational shift.

At Step 510, the position of the distal end 203 of the shaft 202 is determined. In one embodiment, the transformed-impedance position of the distal end 203 of the shaft is determined using the transformed-impedance positions for two of the shaft electrodes 204. The following equation may be used to calculate the transformed-impedance position of the distal end 203 of the shaft 202:

$$P = \frac{E_2 \times S_1 - E_1 \times S_2}{E_2 - E_1} \quad \text{Eq. 1}$$

where P is the transformed-impedance position of the shaft distal end 203, $S_1$ and $S_2$ are the transformed-impedance positions of the two shaft electrodes 204, and $E_1$ and $E_2$ are the mechanical/physical offsets of the corresponding shaft electrodes 204 from the distal end 203 of the shaft 202. An example of a mechanical offset is a distance from the distal end 203 to the shaft electrode 204. Assumptions of Equation (1) include: P, $S_1$, and $S_2$ are on the same line and $S_2$, $S_1$, and the distal end P are proportionally scaled.

At Step 520, a translational shift vector is determined. The translational shift vector is a vector between the transformed-impedance position of the shaft distal end 203 (P, Step 510) and the magnetic position of the shaft distal end 203 determined based on the magnetic position of the EM sensor 206.

At Step 530, the translational shift vector of Step 520 is applied to each electrode 204, 210 to correct transformed impedance-based position of the grid electrodes 210 based on the determined mis-alignment between the magnetic-based position of the shaft distal end 203 and the impedance-based position of the shaft distal end 203. In some embodiments, the translational shift vector is simply added to the transformed-impedance position of the grid electrodes 210 to generate a normalized position of the grid electrodes 210.

At Step 540, a rotational shift vector θ between the transformed-impedance shaft longitudinal axis and the magnetic shaft longitudinal axis is determined. An exemplary equation for Step 540 is:

$$\theta = \arccos(v1 \cdot v2), \quad \text{Eq. 2}$$

where v1 and v2 are the unit vectors representing the transformed-impedance shaft longitudinal axis and magnetic shaft longitudinal axis, respectively, and θ is the rotational shift vector.

At Step 550, the rotational shift vector θ is applied to each electrode 204, 210 to produce an aligned shaft longitudinal axis by aligning the transformed-impedance shaft longitudinal axis with the magnetic shaft longitudinal axis. The rotational shift is performed about the vector normal to v1 and v2.

In some embodiments, the order in which Steps 510, 520, 530, 540, and 550 are performed may be modified. For example, the rotational shift vector θ may be calculated and applied to the grid electrodes 210 (as described at Steps 540, 550), and then the translational shift vector may be determined and applied to the grid electrodes 210.

Referring to FIG. 6, a flowchart of an exemplary method 600 for performing the grid shift compensation as described in Step 440 of method 400 is provided. Method 600 may be executed when the catheter 200 is in either a magnetic primary operation mode or impedance primary operation mode. In some embodiments, if the operation mode of the catheter 200 is magnetic primary, the transformed impedance positions/axes (established in Step 420) are utilized during the execution of method 600. In other embodiments, if the operation mode of the catheter 200 is impedance primary, the impedance positions for grid electrodes 210 are utilized during the execution of method 600. Reference is made to FIGS. 7A-12 to illustrate the various steps described in FIG. 6.

As discussed above, the array 208 can bend relative to the longitudinal axis a, of the shaft 202 (see e.g., FIG. 2). Grid shift compensation compensates for impedance shift—impedance-based position errors introduced by an impedance measurement/tracking system in the measured impedances associated with shaft electrodes 204 and grid electrodes 210. In some embodiments, these errors are introduced as a result of differences in impedances presented by the shaft electrodes 204 relative to the grid electrodes 210, resulting in grid shift errors in the determined locations of the grid electrodes. Grid shift compensation does not compensate for a shift due to movement of the grid, e.g., bending or curving. Rather, grid compensation compensates only for errors introduced as a result of impedance shifts in the impedance-based location of the grid electrodes 210. In some embodiments, grid shift compensation is applied uniformly to each of the plurality of grid electrodes 210. In other embodiments, grid shift compensation may be applied to the grid 208 as a whole. In some embodiments, the grid shift compensation method 600 computes a lateral grid shift vector representing a lateral shift of the grid 208 due to impedance shift (e.g., Steps 610-650), computes a longitudinal grid shift vector representing the longitudinal shift of the grid 208 due to impedance shift (e.g., Step 660), and applies the lateral and longitudinal grid shift vectors to all the grid electrodes 210 to correct the positions of the grid electrodes 210 located on the grid 208 (e.g., Step 670). The lateral grid shift vector is normal to the shaft longitudinal axis and represents the impedance shift of the grid 208 relative to the shaft longitudinal axis. The longitudinal grid shift vector is the shift of the grid 208 relative to a plane normal to the shaft longitudinal axis and represents the impedance shift along the shaft longitudinal axis.

Figures 7A, 7B, 7C:
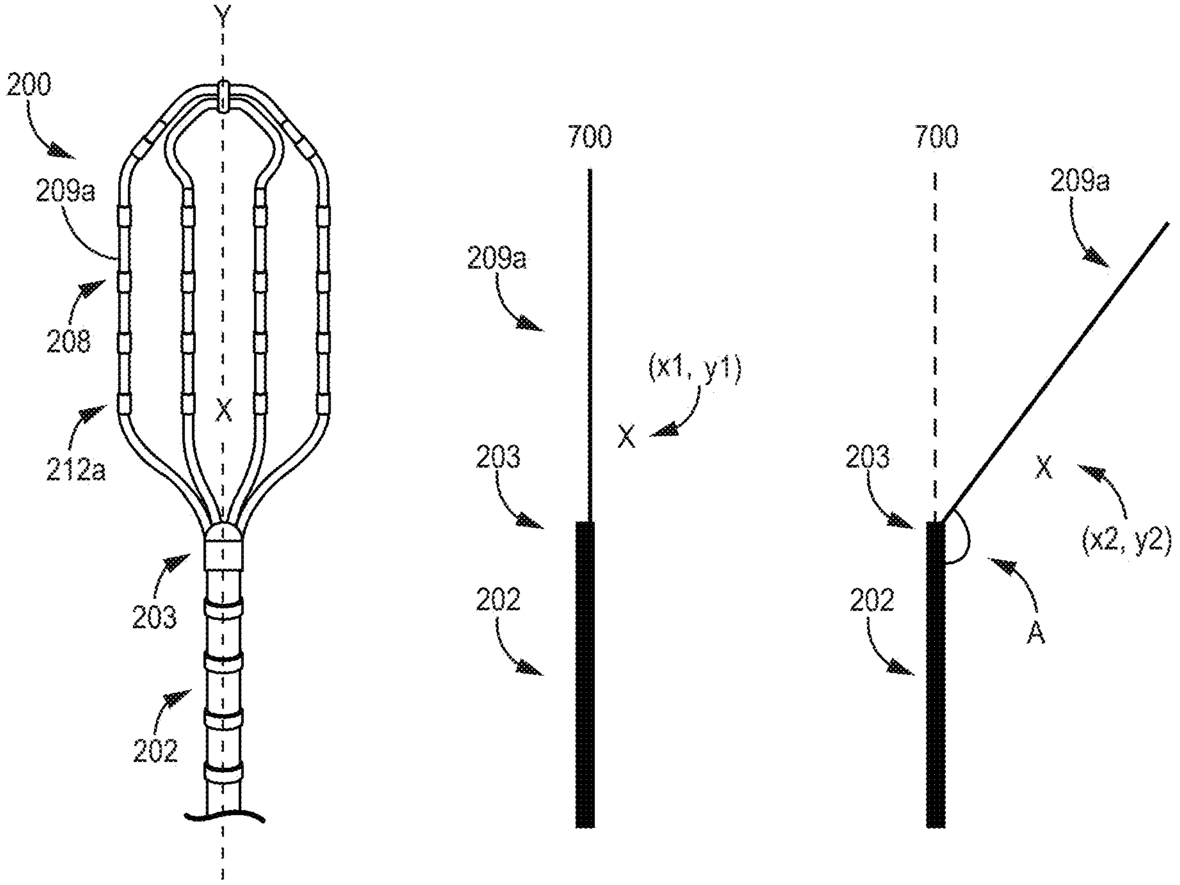
FIG. 7A is a top view of catheter 200 of FIG. 2A, illustrating an electrode array according to some embodiments.
FIG. 7B is a diagrammatic side view of FIG. 2A where the wider solid line represents the catheter shaft and the narrower solid line represents a strut of the array.
FIG. 7C is a diagrammatic view of FIG. 7B illustrating the array at an angle A to the shaft according to some embodiments.

At Step 610, the position (transformed-impedance position or impedance-based position) representing the approximate center of the grid electrodes 210 is established (hereinafter grid center X). In some embodiments, the position of grid center X is calculated based on the average or collective positions of all the grid electrodes 210. In some embodiments, the position of grid center X is calculated based only on the positions of the grid electrodes 210*a* located in the proximal row 212*a* as shown in FIG. 7A. In some embodiments, the transformed-impedance position of the grid electrodes 210*a* in the proximal row 212*a* are utilized to determine the grid center X by virtue of being located closer to the EM sensor 206, and therefore presenting less positional error than grid electrodes 210*b*, 210*c*, 210*d* located more distal from the EM sensor 206. As noted above, when the catheter is in the magnetic primary operating mode the transformed impedance positions are used to calculate the position of grid center X and when the catheter is in the impedance primary operating mode the impedance positions are used to calculate the position of grid center X.

For example, FIGS. 7A-C illustrate the position of the grid center X relative to the distal shaft end 203. FIG. 7A is a top view of catheter 200 of FIG. 2A, illustrating an array 208 that is planar according to some embodiments, and FIGS. 7B-C are side views illustrate a change in the position of grid center X as the grid 208 bends according to some embodiments. In each of these views, the longitudinal axis (impedance axis 700 in this embodiment) of shaft 202 is along the Y-axis. In this example, the position of the grid center X is based on impedance-based or transformed position estimates of the grid electrodes 210*a* located in the proximal row 212*a*. Assuming no impedance or load effect error and/or bending of the struts 209, the impedance-based or transformed position estimates of the grid electrodes 210*a* result in an average position (i.e., the grid center X) being located in the center of the proximal row 212*a* of electrodes 210 on axis Y. However, the introduction of load effect errors on the grid electrodes 210 result in a shift in impedance-based or transformed position estimates of the grid electrodes (in particular with respect to the impedance-based or transformed impedance longitudinal axis defined by the position of shaft electrodes 204). For example, in FIG. 7B the grid center X is offset from the impedance shaft longitudinal axis 700 at position (x1, y1). In response to bending of the array 208 shown in FIG. 7C, the position of grid center X is modified as a result of the bend. For example, the grid center X has coordinates (x2, y2) in FIG. 7C—where y2 is less than y1. In other words, as the array 208 bends, the position of the grid center X moves longitudinally closer to the distal end 203 of the shaft 202 and laterally away from the longitudinal axis of the shaft 202 (impedance shaft longitudinal axis 700 in this example).

Figure 8:
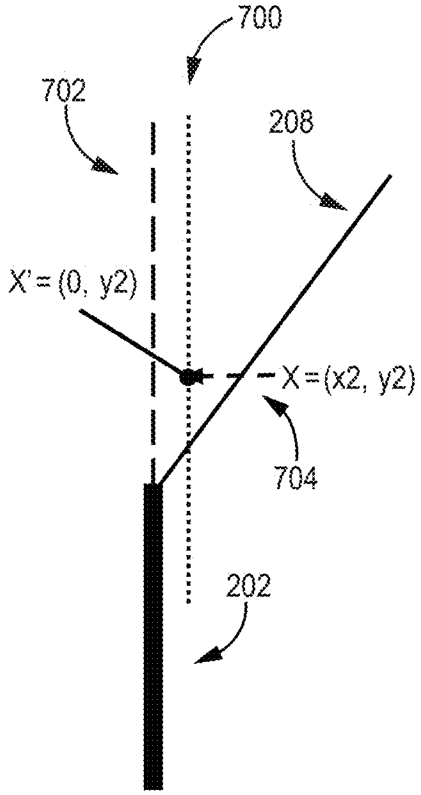
FIG. 8 is a diagram illustrating a geometrical center of an electrode array, and an impedance shaft longitudinal axis positioned to the side of the magnetic shaft longitudinal axis according to some embodiments.

At Step 620, a shift vector 704 representing the shift of the grid center X (established in Step 610) relative to the shaft longitudinal axis is determined. If the grid center X is aligned with the shaft longitudinal axis (as shown in FIG. 7A) then the shift vector 704 is essentially zero. However, both load effect errors and bending of the array 208 will result in the grid center X being shifted relative to the shaft longitudinal axis. For example, in the embodiments shown in FIG. 8 the array 208 is angled/bent relative to the shaft 202, which contributes to the grid center X (position x2, y2) moving to the right relative to the longitudinal axis (in this embodiment, the impedance longitudinal axis 700 is offset or mis-aligned with the magnetic-based longitudinal axis 702 determined by the EM sensor 206). In some embodiments, the shift vector 704 is determined by projecting the grid center X (established in Step 610) onto the shaft longitudinal axis (700 or 702)—X' represents the projected grid center. In this case the projected grid center X' is placed at coordinates (0, y2), assuming that the longitudinal axis is placed at x=0 and the value of y2 remains the same when projecting onto the longitudinal axis. In some embodiments, when the catheter is in impedance primary operation mode, the grid center X is projected onto the impedance shaft longitudinal axis 700, as shown in FIG. 8. In some embodiments, when the catheter is in magnetic primary operation mode, the grid center X is projected onto the magnetic shaft longitudinal axis 702.

Figure 9:
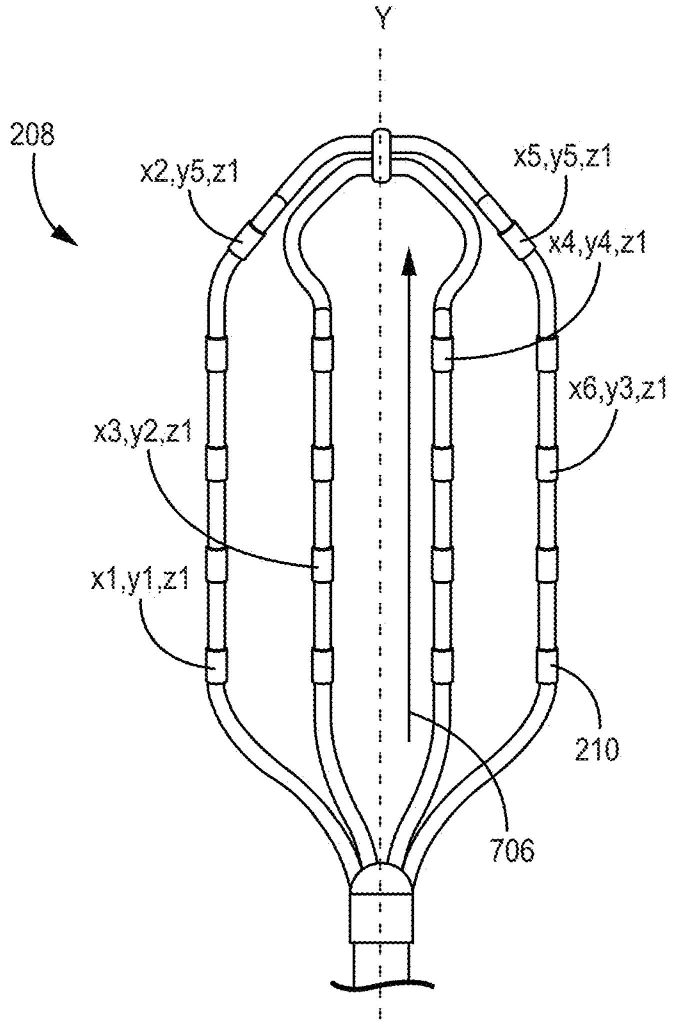
FIG. 9 is a diagram of electrodes arranged in an array and a spline vector according to some embodiments.

At Step 630, the "spline" vector 706 of the grid 208 is computed. A spline vector 706 is an imaginary line in space representing a center spline of the array 208. An example is illustrated in FIG. 9, which is a diagrammatic view of electrodes 210 arranged in a grid 208 with some of the grid electrode x-y-z positions identified according to some embodiments. In one embodiment, an approximated grid spline 706 is determined by applying a linear least-square fit to the impedance/transformed impedance positions (x, y, z) of each grid electrode 210. The location of the grid spline vector 706 relative to array 208 is affected by the roll, pitch, yaw, and curvature experienced by array 208 since a change in the position/orientation of the grid 208 affects the positions of grid electrodes 210. In the example provided in FIG. 9, the spline vector 706 is located to the side of the Y-axis. Although the spline vector 706 in FIG. 9 is illustrated as parallel with the longitudinal axis of the shaft 202, in embodiments in which the array 208 is bent relative to the shaft 202 the spline vector 706 will be oriented at an angle relative to the longitudinal axis of the shaft 202 (either the impedance-based longitudinal axis 700 or the magnetic-based longitudinal axis 702).

Figure 10:
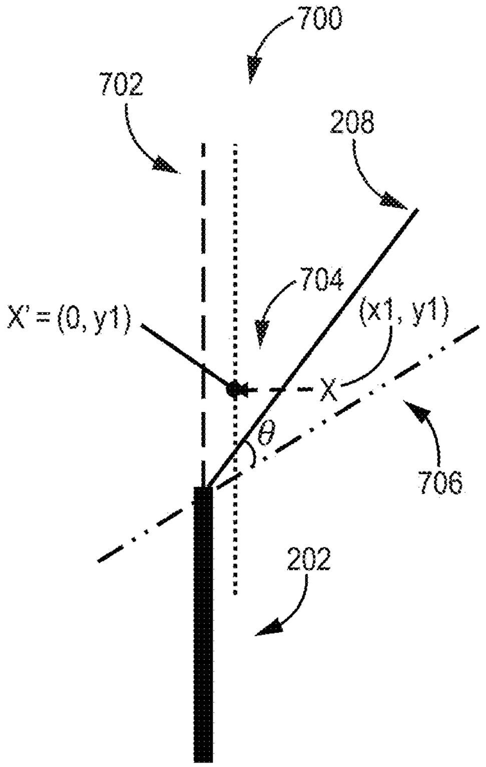
FIG. 10 is a diagrammatic view of FIG. 8 that further includes a grid spline vector according to some embodiments.

At Step 640, the angle θ between the grid spline vector 706 (established in Step 630) and the shaft longitudinal axis is determined. An example of this calculation is illustrated in FIG. 10, which illustrates the shaft 202, an impedance shaft longitudinal axis 700 offset from the magnetic longitudinal axis 702, the array 208, the grid center X, the projected grid center X', the shift vector 704, the angle θ, and the spline vector 706 according to some embodiments. One way to determine angle θ is to compute the dot product of the unit vectors representing the grid spline vector 706 and the shaft longitudinal axis (700 or 702), respectively, e.g., $$\theta = \cos^{-1}\frac{\vec{A}\cdot\vec{B}}{|\vec{A}||\vec{B}|},$$

where $\vec{A}$ is the unit vector of spline vector 706 and $\vec{B}$ is the unit vector of the shaft longitudinal axis (700 or 702).

Figure 11A:
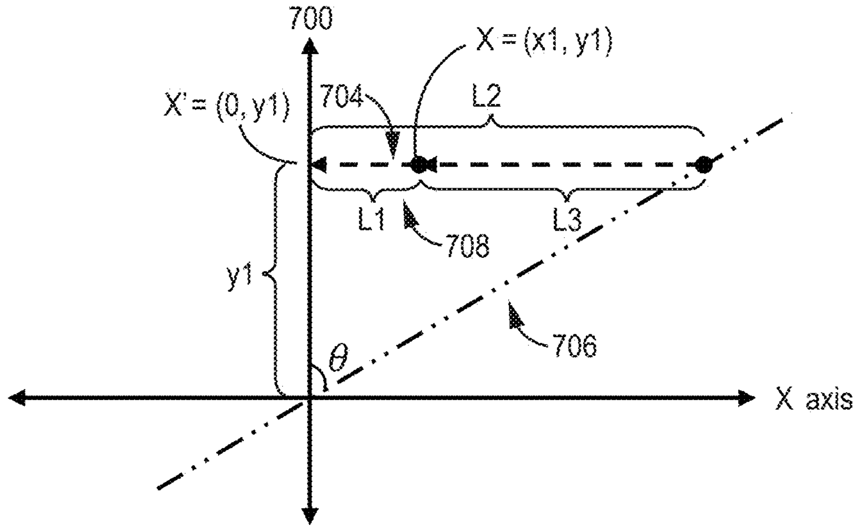
FIGS. 11A and 11B are diagrams illustrating the use of trigonometry to determine the lateral grid shift vector according to some embodiments.
Figure 11B:
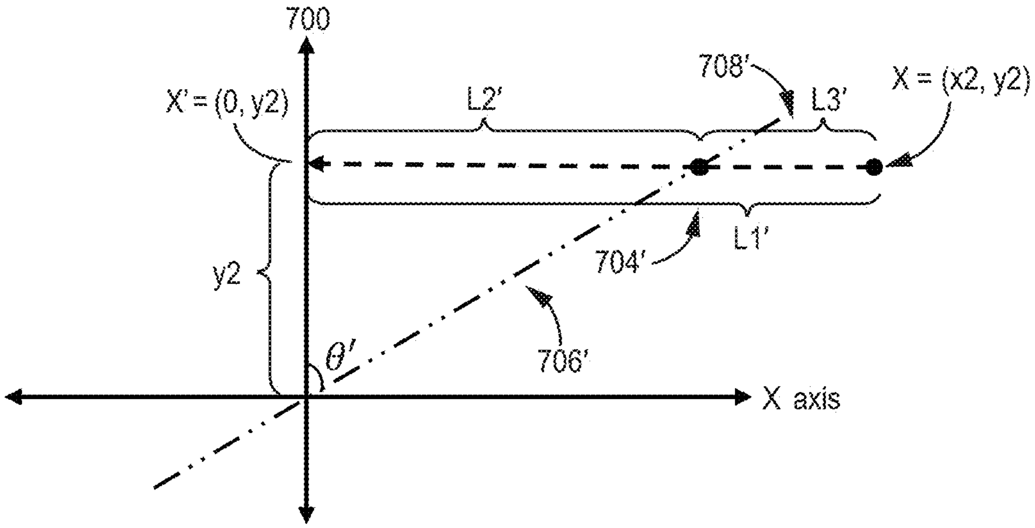

At Step 650, a lateral grid shift vector 708 is determined using the shift vector 704 (established in Step 620) and the angle θ (established in Step 640). The lateral grid shift vector 708 represents the shift due to the loading effect on impedance, while removing the effect of the array 208 being bent relative to the shaft 202. For example, FIGS. 11A and B are diagrams illustrating 2D trigonometry that may be used to determine the lateral grid shift vector 708 for a planar array 208 according to some embodiments. In the diagrams, the intersection of the shaft longitudinal axis, e.g., shaft axis 700, and the spline vector 706 is positioned at the origin of an x-y plane with the impedance shaft axis 700 along the Y-axis and the spline vector 706 at an angle θ to the Y-axis. As shown in FIG. 10, the intersection of the shaft longitudinal axis and the spline vector 706 may be at the distal end of the shaft, e.g., shaft axis 702 or offset from the distal end of the shaft, e.g., shaft axis 700. FIG. 11A illustrates an example where the grid center X is positioned closer to the shaft longitudinal axis (700 or 702) than the spline vector 706 and FIG. 11B illustrates an example where the grid center X is positioned farther away from the shaft longitudinal axis (700, or 702) than the spline vector 706. In both diagrams, the spline vector 706 forms the hypotenuse of a right triangle positioned at the origin of an x-y plane. In FIG. 11A, the shift vector 704 (established in Step 620) forms only a part of the side opposite angle θ, while in FIG. 11B, shift vector 704' extends the entire side opposite angle θ and some additional length not included in the side opposite angle θ.

With respect to FIG. 11B, the position of grid center X is represented as the point (x2, y2) and the position of projected grid center X' is represented as the point (0, y2). The shift vector 704' represents the shift of the grid center X from the impedance longitudinal axis 700 and has a length L1'. The length of triangle leg opposite angle θ has a length L2' that is calculated as: L2' y tan(0) and represents the shift due to the bend of the array 208' as evidenced by spline 706'. The portion of the shift attributable to load effect is the length L2' minus the length of the shift vector 704', expressed as L3'=L2'–L1', wherein L3' represents the lateral shift vector. In this example, the length L3' is negative, and therefore would have a direction in the negative x direction. Thus, the impedance-based position of a grid electrode 210 may be modified to compensate for load effect shifts (i.e., impedance shifts) by adding the lateral grid shift vector 708' to each grid electrode location. In this case, the lateral grid shift vector 708' would result in a shift of grid electrode position to the left (negative x-axis) by a length L3'.

With respect to the embodiment shown in FIG. 11A, the same steps are performed. The position of grid center X is represented as the point (x1, y1) and the position of projected grid center X' is represented as the point (0, y1). The shift vector 704 represents the shift of the grid center X from the impedance longitudinal axis 700 and has a length L1. The length of triangle leg opposite angle θ has a length L2 that is calculated as: L2 y tan(B) and represents the shift due to the bend of the array 208 as evidenced by spline 706. The portion of the shift attributable to load effect is the length L2 minus the length of the shift vector 704, expressed as L3=L2–L1, wherein L3 represents the lateral shift vector. In this example, the length L3 is positive, and therefore would have a direction in the positive x direction. Thus, the impedance-based position of a grid electrode 210 may be modified to compensate for load effect shifts (i.e., impedance shifts) by adding the lateral grid shift vector 708 to each grid location. In this case, the lateral grid shift vector 708 would result in a shift of grid electrode position to the right (positive x-axis) by a length L3.

Figure 12:
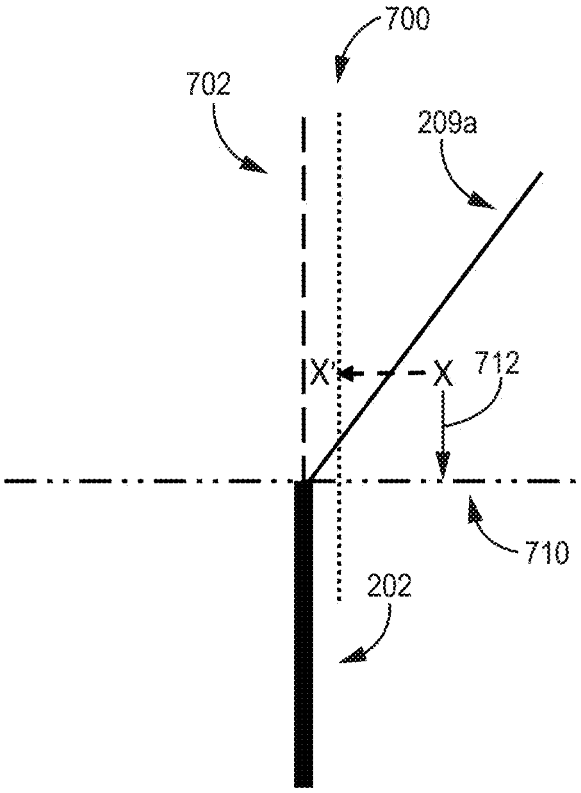
FIG. 12 is a diagram illustrating the establishment of a longitudinal grid shift vector according to some embodiments.

At Step 660, a longitudinal grid shift vector 712 representing the shift of the grid center X (established in Step 610) relative to a plane 710 is determined. Plane 710 is normal to the shaft longitudinal axis 700, 702 and includes the distal shaft end 203. In one aspect, longitudinal shift introduced by bending the array 208 is accounted for by using the grid center X to determine the longitudinal shift vector 712. In other words, the longitudinal grid shift vector 712 only represents the longitudinal shift introduced by an impedance measurement/tracking system. FIG. 12 is a diagrammatic view of the impedance shaft longitudinal axis 700 offset from the magnetic shaft longitudinal axis 702, the grid center X, the projected grid center X', and a longitudinal grid shift vector 712. Grid center X may be positioned above plane 710, as illustrated in FIG. 12, or positioned below plane 710.

At Step 670, the lateral grid shift vector 706 (established in Step 650) and longitudinal grid shift vector 712 (established in Step 660), are applied to each of the grid electrodes 210 to adjust the positions of the electrodes 210. The lateral grid shift vector 706 shifts the position of grid electrodes 210 left or right relative to the longitudinal shaft axis 700, 702. The longitudinal grid shift vector 712 shifts the position of the electrodes either up or down along the longitudinal shaft axis 700, 702—a grid center X positioned below plane 710 will shift grid electrodes 210 upward and a grid center X positioned above plane 710 will shift grid electrodes 210 downward. The lateral grid shift vector 706 and the longitudinal grid shift vector 712 may be described as a decomposition of a grid shift vector.

In some embodiments, the order in which Steps 610, 620, 630, 640, 650, 660, 670 are performed may be modified. For example, the spline vector 704 and angle θ (as described at Steps 630, 640), may be determined before the grid center X and shift vector 704 (as described at Steps 610, 620). As another example, the longitudinal grid shift vector 712 (as described in Step 660), may be determined anytime after Step 610. As a further example, lateral grid shift vector 706 and the longitudinal grid shift vector 712 may be applied to the grid electrodes 210 once they are determined rather than at the end of the method (see Step 670).

Figure 14A:
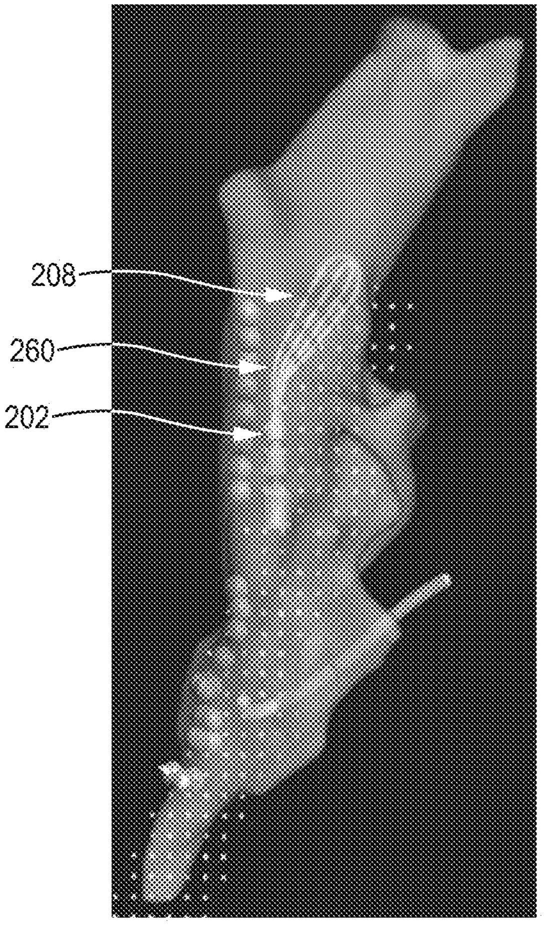
FIGS. 14A and 14B are views of a catheter with a grid electrode before (FIG. 14A) and after (FIG. 14B) execution of method 400 illustrated in FIG. 4.
Figure 14B:
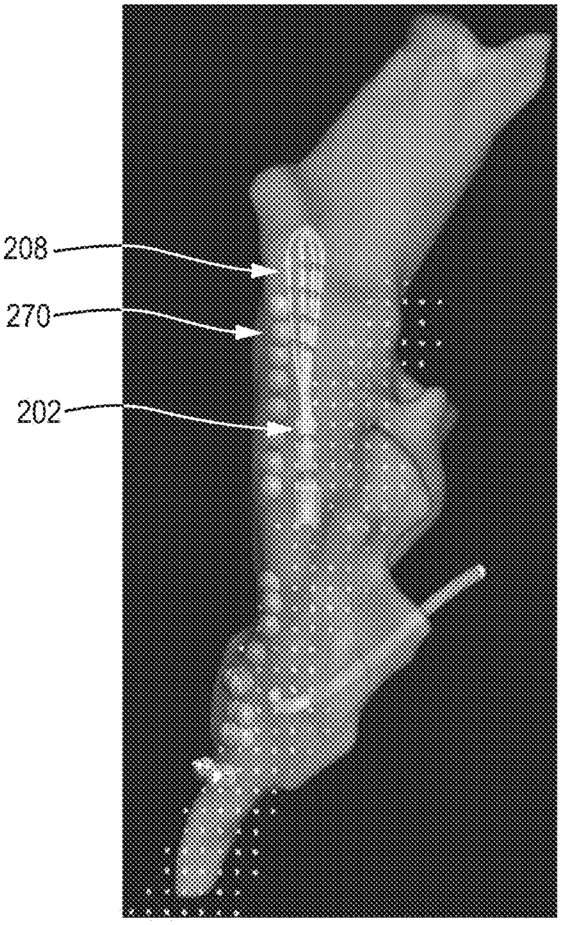

FIGS. 14A and 14B show the images of a catheter with an array/grid 208 of electrodes 210 before and after the application of method 400. As discussed above, an impedance shift causes the grid 208 to have a spatula shape 250. Before the application of method 400 an incorrect shape 260 for the array 208 is generated/displayed (see e.g., FIGS. 13 and 14A). In this example, the array 208 is incorrectly depicted as being at an angle to shaft 202. After the application of method 400, a correct shape 270 for the array 208 is generated/displayed—array 208 extends straight from the distal end of the shaft 202.

In some embodiments, the results of method 400 are used to generate and display an image of the array 208 and/or the catheter 200 (see e.g., FIG. 14B). In other embodiments, the positions of the electrodes 210 on the array 208 generated by method 400 are used to generate a map of the heart, e.g., a voltage map or a conduction map.

The terms "proximal" and "distal" used herein are with reference to a clinician utilizing the catheter where "proximal" is closer to the clinician than "distal".

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method in an impedance-based location system, the method comprising:
- determining a geometrical center for a grid of electrodes attached to a distal end of a catheter shaft, the catheter shaft further comprising at least one shaft electrode and an electromagnetic sensor;
- determining a first shift vector from the geometrical center to a longitudinal axis of the catheter shaft;
- determining a spline vector for the grid of electrodes;
- determining an angle between the spline vector and the longitudinal axis;
- determining a lateral grid shift vector using the first shift vector and the angle;
- determining a longitudinal grid shift vector extending from the geometrical center to a plane normal to the longitudinal axis and extending through the distal end; and
- applying the lateral grid shift vector and the longitudinal grid shift vector to each electrode of the grid of electrodes to correct errors in impedance-based positions introduced by impedance shifts resulting from impedance loading effects.

2. The method of claim 1, wherein determining the geometrical center comprises determining the geometrical center of a proximal row of electrodes of the grid.

3. The method of claim 1, wherein determining the first shift vector from the geometrical center to the longitudinal axis comprises projecting the geometrical center onto the longitudinal axis.

4. The method of claim 1, wherein determining the spline vector comprises applying a linear least square fit to a position of each electrode of the grid of electrodes.

5. The method of claim 1, the method further comprising:
- determining a translational shift vector representing a shift between a transformed impedance position for the distal end and a magnetic position for the distal end;
- determining a rotational shift vector for a shift between a transformed impedance longitudinal axis and a magnetic longitudinal axis; and
- applying the translational shift vector and the rotational shift vector to each electrode of the grid of electrodes.

6. The method of claim 1, further comprising generating an image of the grid of electrodes.

7. The method of claim 1, further using the grid of electrodes to map electrical activity in a heart, the method further comprising generating a map of electrical activity in a heart.

8. A non-transitory computer readable medium with instructions for a method of compensating for impedance loading effect in an impedance-based location system, the method comprising:
- determining a geometrical center for a grid of electrodes attached to a distal end of a catheter shaft, the catheter shaft further comprising at least one shaft electrode and an electromagnetic sensor;
- determining a first shift vector from the geometrical center to a longitudinal axis of the catheter shaft;
- determining a spline vector for the grid of electrodes;
- determining an angle between the spline vector and the longitudinal axis;
- determining a lateral grid shift vector using the first shift vector and the angle;
- determining a longitudinal grid shift vector extending from the geometrical center to a plane normal to the longitudinal axis and extending through the distal end; and
- applying the lateral grid shift vector and the longitudinal grid shift vector to each electrode of the grid of electrodes to correct errors in impedance-based positions introduced by impedance shifts resulting from impedance loading effects.

9. The computer readable medium of claim 8, wherein determining the geometrical center comprises determining the geometrical center of a proximal row of electrodes of the grid.

10. The computer readable medium of claim 8, wherein determining the first shift vector from the geometrical center to the longitudinal axis comprises projecting the geometrical center onto the longitudinal axis.

11. The computer readable medium of claim 8, wherein determining the spline vector comprises applying a linear least square fit to a position of each electrode of the grid of electrodes.

12. The computer readable medium of claim 8, the method further comprising:
- determining a translational shift vector representing a shift between a transformed impedance position for the distal end and a magnetic position for the distal end;
- determining a rotational shift vector for a shift between a transformed impedance longitudinal axis and a magnetic longitudinal axis; and
- applying the translational shift vector and the rotational shift vector to each electrode of the grid of electrodes.

13. The computer readable medium of claim 8, the method further comprising generating an image of the grid of electrodes.

14. The computer readable medium of claim 8, the method further comprising generating a map of electrical activity in a heart.

15. A system with a controller that performs the steps of a method of compensating for impedance loading effect in an impedance-based location system, the steps comprising:

determining a geometrical center for a grid of electrodes attached to a distal end of a catheter shaft, the catheter shaft further comprising at least one shaft electrode and an electromagnetic sensor;

determining a first shift vector from the geometrical center to a longitudinal axis of the catheter shaft;

determining a spline vector for the grid of electrodes;

determining an angle between the spline vector and the longitudinal axis;

determining a lateral grid shift vector using the first shift vector and the angle;

determining a longitudinal grid shift vector extending from the geometrical center to a plane normal to the longitudinal axis and extending through the distal end; and applying the lateral grid shift vector and the longitudinal grid shift vector to each electrode of the grid of electrodes to correct errors in impedance-based positions introduced by impedance shifts resulting from impedance loading effects.

16. The system of claim 15, wherein determining the geometrical center comprises determining the geometrical center of a proximal row of electrodes of the grid.

17. The system of claim 15, wherein determining the shift from the geometrical center to the longitudinal axis comprises projecting the geometrical center onto the longitudinal axis.

18. The system of claim 15, wherein determining a spline vector comprises applying a linear least square fit to positions of the grid electrodes.

19. The system of claim 15, the method further comprising:

determining a translational shift vector representing a shift between a transformed impedance position for the distal end and a magnetic position for the distal end;

determining a rotational shift vector for a shift between a transformed impedance longitudinal axis and a magnetic longitudinal axis; and applying the translational shift vector and the rotational shift vector to each electrode of the grid of electrodes.

20. The system of claim 15, the steps further comprising generating an image of the grid of electrodes.

* * * * *